United States Patent [19]
Oh et al.

[11] Patent Number: 5,360,528
[45] Date of Patent: Nov. 1, 1994

[54] WIDE RANGE OXYGEN SENSOR

[75] Inventors: Seajin Oh, Palo Alto; Jose Joseph, Menlo Park, both of Calif.; Earl W. Lankheet, Grand Blanc, Mich.

[73] Assignee: General Motors Corporation, Detroit, Mich.

[21] Appl. No.: 916,555

[22] Filed: Jul. 20, 1992

[51] Int. Cl.$^5$ ......................................... G01N 27/419
[52] U.S. Cl. ................... 204/425; 204/192.1; 204/412; 204/426; 204/427; 427/569
[58] Field of Search ................... 204/153.18, 421–429

[56] References Cited

U.S. PATENT DOCUMENTS

| | | | |
|---|---|---|---|
| 4,264,425 | 4/1981 | Kimura et al. | 204/425 |
| 4,272,329 | 6/1981 | Hetrick et al. | 204/425 |
| 4,298,573 | 11/1981 | Fujishiro | 204/425 |
| 4,302,312 | 11/1981 | Ishizani et al. | 204/425 |
| 4,487,680 | 12/1984 | Logothetis et al. | 204/426 |
| 4,559,126 | 12/1985 | Mase et al. | 204/425 |
| 4,570,479 | 2/1986 | Sakurai et al. | 73/116 |
| 4,668,374 | 5/1987 | Bhagat et al. | 204/412 |
| 4,724,061 | 2/1988 | Nyberg | 204/412 |
| 4,810,350 | 3/1989 | Mantese et al. | 204/412 |
| 4,839,018 | 6/1989 | Yamada et al. | 204/425 |
| 4,863,584 | 9/1989 | Kojima et al. | 204/425 |
| 4,980,044 | 12/1990 | Ker | 204/426 |
| 5,089,113 | 2/1992 | Logothetis et al. | 204/425 |
| 5,124,021 | 6/1992 | Kaneyasu et al. | 204/425 |
| 5,178,744 | 1/1993 | Nakazawa et al. | 204/425 |

FOREIGN PATENT DOCUMENTS

| | | |
|---|---|---|
| 0052542 | 5/1982 | European Pat. Off. . |
| 0138170 | 4/1985 | European Pat. Off. . |
| 0172746 | 2/1986 | European Pat. Off. . |
| 3543759 | 10/1986 | Germany . |

OTHER PUBLICATIONS

European Search Report No. EP 93 20 1944 dated 07-Oct.-93 corres to U.S. Ser. No. 07/916,555.

S. Oh and M. Madou, "Planar-Type, Gas-Diffusion-Controlled Oxygen Sensor Fabricated by the Plasma Spray Method", 4th International Meeting on Chemical Sensors, Sep. 1992.

T. Usui, A. Asada, M. Nakazawa and H. Osanai, "Gas Polarographic Oxygen Sensor Using an Oxygen/Zirconia Electrolyte", *J. Electrochem Soc.*, vol. 136, No. 2, (Feb. 1989) pp. 534–542.

H. Dietz, "Gas-Diffusion-Controlled Solid-Electrolyte Oxygen Sensors", *Solid State Ionics*, 6 (1982) pp. 175–183.

A. S. Ioannou and W. C. Maskell, "Characterization of Amperometric Zirconia Oxygen Sensors Prepared Using Planar Thick Film Technology", to be published in Proc. 8th Solid State Ionic Conference, Lake Louise (1991).

(List continued on next page.)

*Primary Examiner*—T. Tung
*Attorney, Agent, or Firm*—Robert J. Wallace; Domenica N. S. Hartman

[57] ABSTRACT

A wide range oxygen sensor is provided which operates partially in the diffusion limited current mode to provide an output which is proportional to the oxygen partial pressure in a gas mixture which is sensed, such as the exhaust gas of an automotive internal combustion engine. The wide range oxygen sensor is constructed to have a planar structure with a single solid electrolyte layer that is shared by electrochemical storage, pumping and reference cells and which is deposited using known thermal deposition techniques. As a result, the wide range oxygen sensor of the present invention is characterized as being relatively low cost and readily producible under mass production conditions. Moreover, the wide range oxygen sensor is capable of rapidly and accurately sensing the exhaust gas oxygen partial pressure while the engine is operating in either the fuel-rich or fuel-lean condition to enable the evaluation of the air-to-fuel ratio of the precombustion fuel mixture.

16 Claims, 5 Drawing Sheets

OTHER PUBLICATIONS

K. Saji, "Characteristics of Limiting Current-Type Oxygen Sensor", *J. Electrochem. Soc.*, vol. 134 (Oct. 1987) pp. 2430–2435.

M. Scagliotti et al., "Plasma-Sprayed Zirconia Electrolytes", Solid State Ionics, 28–30 (1988) pp. 1766–1769.

E. Logothetis, "Air-to-Fuel Sensors Based on Oxygen Pumping", Ceram. Eng. Sci. Proc., 8 [9–10] (1987) pp. 1058–1073.

K. Saji, "Characteristics of Limiting Current-Type Oxygen Sensor", J. Electrochem. Soc. 134, 10 (1987) pp. 2430–2435.

S. Oh et al., "Multilayer Ionic Devices Fabricated By Plasma Spray Method", 8th Solid State Ionic Conf., Oct. Canada (1991) pp. 1–9.

Vassell et al., "Extended Range Air-to-Fuel Ratio Sensor", SAE Paper No. 841250 (1984), pp. 1–7.

WIDE RANGE OXYGEN SENSOR

The present invention generally relates to automotive exhaust gas oxygen sensors of the solid electrolyte, electrochemical type. More particularly, this invention relates to thin film internal reference solid electrolyte oxygen sensors which are capable of rapid linear response to both lean and rich fuel conditions, and which are further characterized by being formed in a planar configuration by successive deposition of suitable materials on an inert substrate.

BACKGROUND OF THE INVENTION

Gas sensors are used in a variety of applications which require qualitative and quantitative analysis of gases. In the automotive industry, it is well known that the oxygen concentration in the exhaust gas of an engine has a direct relationship to the air-to-fuel ratio of the fuel mixture which is supplied to the engine. As a result, oxygen gas sensors are used in automotive internal combustion control systems to provide accurate oxygen concentration measurements of automobile exhaust gases for determination of optimum combustion conditions, maximization of fuel economy, and management of exhaust emissions. To be useful, oxygen sensors should have a rapid response time at temperatures ranging between about −40° C. and 800° C.

As illustrated in U.S. Pat. No. 3,844,920 to Burgett et al., the electrochemical type of oxygen sensor typically used in automotive applications utilizes a thimble-shaped electrochemical galvanic cell operating in the potentiometric mode to determine, or sense, the relative amounts of oxygen present in an automobile engine's exhaust. This type of oxygen sensor includes an ionically conductive solid electrolyte material, typically yttria stabilized zirconia, a porous electrode coating on the sensor's exterior which is exposed to the exhaust gases, and a porous electrode coating on the sensor's interior which is exposed to a known concentration of reference gas. The individual components are typically fabricated by conventional processes such as molding, grinding and high temperature firing.

The gas concentration gradient across the solid electrolyte produces a galvanic potential which is related to the differential of the partial pressures of the gas at the two electrodes according to the Nernst equation:

$$E = AT \ln(P_1/P_2)$$

where E is the galvanic voltage, T is the absolute temperature of the gas, $P_1/P_2$ is the ratio of the oxygen partial pressures of the reference gas at the two electrodes, and $A = R/4F$, where R is the universal gas constant and F is the Faraday constant.

Currently, these potentiometric oxygen sensors are employed in the exhaust gas system of an internal combustion engine to determine qualitatively whether the engine is operating at either of two conditions: (1) a fuel-rich or (2) a fuel-lean condition, as compared to stoichiometry. After equilibration, the exhaust gases created by engines operating at these two operating conditions have two widely different oxygen partial pressures. This information is provided to an air-to-fuel ratio control system which attempts to provide an average stoichiometric air-to-fuel ratio between these two extreme conditions. At the air-to-fuel stoichiometric point, the oxygen concentration changes by several orders of magnitude. Accordingly, potentiometric oxygen sensors are able to qualitatively indicate whether the engine is operating in the fuel-rich or fuel-lean condition, without providing more specific information as to what is the actually air-to-fuel ratio.

Current oxygen sensors which operate in the aforementioned potentiometric mode are sufficiently sensitive to operate satisfactorily about the fstoichiometric point for purposes of indicating whether the engine is operating in the fuel-rich or fuel-lean condition. However, because their output voltage is a function of the natural log of the oxygen partial pressure ratio, a potentiometric sensor does not produce an output that is useful for determining the air-to-fuel ratio at operating conditions away from the stoichiometric point.

Due to increasing demands for improved fuel utilization and emissions control, more recent emphasis has been on wide range oxygen sensors capable of accurately determining the oxygen partial pressure in exhaust gas for internal combustion engines operating under both fuel-rich and fuel-lean conditions. Such conditions require an oxygen sensor which is capable of rapid response to changes in oxygen partial pressure by several orders of magnitude, while also having sufficient sensitivity to accurately determine the oxygen partial pressure in both the fuel-rich and fuel-lean conditions. The output of a potentiometric oxygen sensor does not provide sufficient resolution to quantify small changes in exhaust gas oxygen partial pressures when operating away from the stoichiometric point, and therefore cannot accurately determine the air-to-fuel ratio under fuel-rich or fuel-lean conditions.

The prior art has suggested that oxygen sensors which produce an output proportional to the air-to-fuel ratio may offer significant performance advantages for future engine control systems. As taught by U.S. Pat. No. 4,863,584 to Kojima et al., U.S. Pat. No. 4,839,018 to Yamada et al., U.S. Pat. No. 4,570,479 to Sakurai et al., and U.S. Pat. No. 4,272,329 to Hetrick et al., an oxygen sensor which operates in the diffusion limited current mode produces such a proportional output which provides sufficient resolution to determine the air-to-fuel ratio under fuel-rich or fuel-lean conditions. Generally, diffusion limited current oxygen sensors have a pumping cell and an oxygen storage cell for generating an internal oxygen reference. A constant electromotive force is maintained between the storage cell and the pumping cell so that the magnitude and polarity of the pumping current can be detected as being indicative of the exhaust gas composition.

While the above diffusion limited current oxygen sensors generally provide satisfactory performance, there remains the need to further improve the construction of these devices to reduce their costs and make them more readily producible under mass production conditions. Specifically, each of the oxygen sensors taught by the above prior art relies upon structure which forms a chamber or gap, features which complicate processing and assembly in mass production.

Thus, it would be desirable to provide an oxygen sensor for an internal combustion engine operating within both the fuel-rich and fuel-lean conditions which is extremely sensitive and capable of rapid, precise, and absolute oxygen concentration measurements, while also being amenable to mass production.

SUMMARY OF THE INVENTION

It is an object of this invention to provide an oxygen sensor for an internal combustion engine which is capable of accurately determining the air-to-fuel ratio over a wide range of operating conditions including both fuel-rich and fuel-lean, while also being constructed to be more readily manufactured under mass production processing conditions.

It is a further object of this invention that such a wide-range oxygen sensor operate at least partially in the diffusion limited current mode so as to provide an output which is proportional to the oxygen partial pressure in the engine's exhaust gas.

Lastly, it is still a further object of this invention that such a wide range oxygen sensor be processed using thermal spray methods, and particularly plasma spray methods, in accordance with this invention so as to promote its mass producibility.

In accordance with a preferred embodiment of this invention, these and other objects and advantages are accomplished as follows.

According to the present invention, there is provided an oxygen sensor for an internal combustion engine which is capable of accurately determining the air-to-fuel ratio under both fuel-rich and fuel-lean operating conditions—what is termed a wide range oxygen sensor. The oxygen sensor has a planar construction produced by plasma spray deposition methods which facilitates manufacture of the oxygen sensor under mass production processing conditions. The oxygen sensor includes a suitable substrate, an electrochemical storage cell and an electrochemical pumping cell disposed on the substrate in spaced-apart relation to each other, and an electrochemical reference cell formed between the storage and pumping cells. The electrochemical storage cell and the electrochemical pumping cell share a solid electrolyte layer which facilitates processing and reduces manufacturing costs. "Ionic cross-talk" between the electrochemical storage cell and the electrochemical pumping cell is held to an insignificant level by the particular geometry of the solid electrolyte layer.

The electrochemical storage cell has a pair of electrodes disposed on opposite sides of the solid electrolyte layer. An oxygen storage layer is disposed on the substrate and contacts a lower of the two electrodes. The upper electrode contacts the exhaust gas to be measured. The electrochemical storage cell is driven by a constant current source so as to pump oxygen into the oxygen storage layer thereby maintaining a predetermined oxygen partial pressure therein. The predetermined oxygen partial pressure serves as a reference partial pressure for the oxygen sensor, and is preferably within at least one order of magnitude from one atmosphere.

The electrochemical pumping cell also has a pair of electrodes positioned on opposite sides of the solid electrolyte layer. In a manner similar to the oxygen storage layer of the electrochemical storage cell, the electrochemical pumping cell has a diffusion layer disposed on the substrate which contacts a lower of the electrochemical pumping cell's two electrodes. Again, the upper electrode contacts the exhaust gas to be measured. During operation, oxygen and reducing gases in the exhaust gas are able to diffuse laterally into the diffusion layer. The electrochemical pumping cell is driven by a variable voltage source connected to its electrodes so as to pump oxygen into and out of the diffusion layer. As described more fully below, it is the current flow resulting from this variable voltage source which is measured and indicative of the exhaust gas content. Oxygen is pumped into or out of the diffusion layer, depending upon the oxygen partial pressure within the diffusion layer which is predisposed to correspond to the oxygen partial pressure of the exhaust gas.

The electrochemical reference cell is formed between the lower electrodes of the electrochemical storage and pumping cells, and serves to monitor the oxygen partial pressure in the diffusion layer of the electrochemical pumping cell relative to the predetermined oxygen partial pressure in the oxygen storage layer of the electrochemical storage cell. The electrochemical reference cell produces a voltage output based upon the potential difference between the lower electrodes which is created by the difference in oxygen partial pressure between the diffusion cell and the oxygen storage cell. This potential difference is sought to be maintained at a level corresponding to the air/fuel stoichiometric point. This voltage output can then be used as feedback to the electrochemical pumping cell's variable voltage source such that the electrochemical pumping cell is directed to maintain an oxygen partial pressure in the diffusion layer at a level approximately equal to the air/fuel stoichiometric point. As a result, an ionic current flows through the electrochemical pumping cell which is proportional to the oxygen concentration in the exhaust gas. In addition, the direction of the current flow is dependent upon whether the air/fuel mixture is fuel-rich or fuel-lean. If the air/fuel mixture is fuel-rich (i.e., oxygen-poor), the electrochemical pumping cell is forced to pump oxygen into the diffusion layer, while a fuel-lean air/fuel mixture (i.e., oxygen-rich) results in the electrochemical pumping cell being forced to pump oxygen out of the diffusion layer.

The solid electrolyte layer is preferably an yttria stabilized zirconia (YSZ) material which permits the transfer of oxygen ions therethrough under the influence of the electrical circuits. The oxygen storage and diffusion layers are preferably porous layers which permit the diffusion of oxygen molecules therethrough. Preferably, the oxygen storage and diffusion layers are both screen printed on the substrate. The electrodes are each preferably formed of porous platinum using known sputtering methods. Finally, the substrate is preferably a dense substrate which prevents oxygen ions and molecules from diffusing out through the base of the oxygen sensor.

The construction of the oxygen sensor and processing method of this invention used to build the oxygen sensor both serve to reduce manufacturing costs, while also making the oxygen sensor more readily producible under mass production conditions. The processing steps include depositing a pair of spaced-apart porous layers, corresponding to the oxygen storage layer of the electrochemical storage cell and the diffusion layer of the electrochemical pumping cell, onto the dense substrate using known screen printing methods and firing. If the dense substrate is formed from dense YSZ, an insulating layer of porous ceramic is then deposited by plasma spray deposition everywhere on the substrate except on the porous layers. A first pair of porous platinum electrodes are then sputtered onto the insulating layer such that each of the electrodes is in contact with a corresponding one of the porous layers. Two narrow aluminum oxide layers are then formed by plasma spray methods to determine the exposed area of the first electrodes and also to prevent leakage of oxygen at the first electrodes. The solid electrolyte layer is then formed by plasma spray deposition methods to cover essentially all of the electrodes except for portions left bare for serving as electrical contacts to external electronic circuits. The thickness of the electrolyte layer is limited relative to the distance between the porous YSZ layers so as to minimize the ionic cross-talk between the two porous YSZ layers. Finally, a second pair of porous platinum electrodes is sputtered onto the solid electrolyte layer such that each is in ionic communication with a corresponding one of the first pair of electrodes through the solid electrolyte layer.

Using this processing method, the oxygen sensor provides a relatively low-cost, high performance oxygen sensor whose output is proportional to the oxygen partial pressure in the exhaust gas. The horizontal structure is a more practical construction for wide range oxygen sensors in that the structure does not require intricate reference chambers or the vertical assembly of many layers. Correspondingly, the oxygen sensor is capable of sensing small changes in the oxygen partial pressure of the exhaust gas corresponding to operation of an engine in either the fuel-lean or fuel-rich condition. Finally, whether the engine is operating fuel-lean or fuel-rich will be exhibited by the direction of current flow through the electrochemical pumping cell.

Other objects and advantages of this invention will be better appreciated from the following detailed description.

BRIEF DESCRIPTION OF THE DRAWINGS

The above and other advantages of this invention will become more apparent from the following description taken in conjunction with the accompanying drawing wherein.

DETAILED DESCRIPTION OF THE INVENTION

A wide range oxygen sensor is provided which operates partially in the diffusion limited current mode to provide an output which is proportional to the oxygen partial pressure in a gas mixture which is sensed, such as the exhaust gas of an automotive internal combustion engine. Moreover, the wide range oxygen sensor is capable of rapidly and accurately sensing the exhaust gas oxygen partial pressure while the engine is operating in either the fuel-rich or fuel-lean condition so as to determine the air-to-fuel ratio of the precombustion fuel mixture. The wide range oxygen sensor is constructed to have a planar structure that facilitates its manufacture using known thermal deposition techniques. As a result, the wide range oxygen sensor of the present invention is characterized as being of relatively low cost and readily producible under mass production conditions. The wide range oxygen sensor is also rugged for operating in the severe environment of an automobile's exhaust system.

Figures 7, 8, 9, 10, 11, 12:
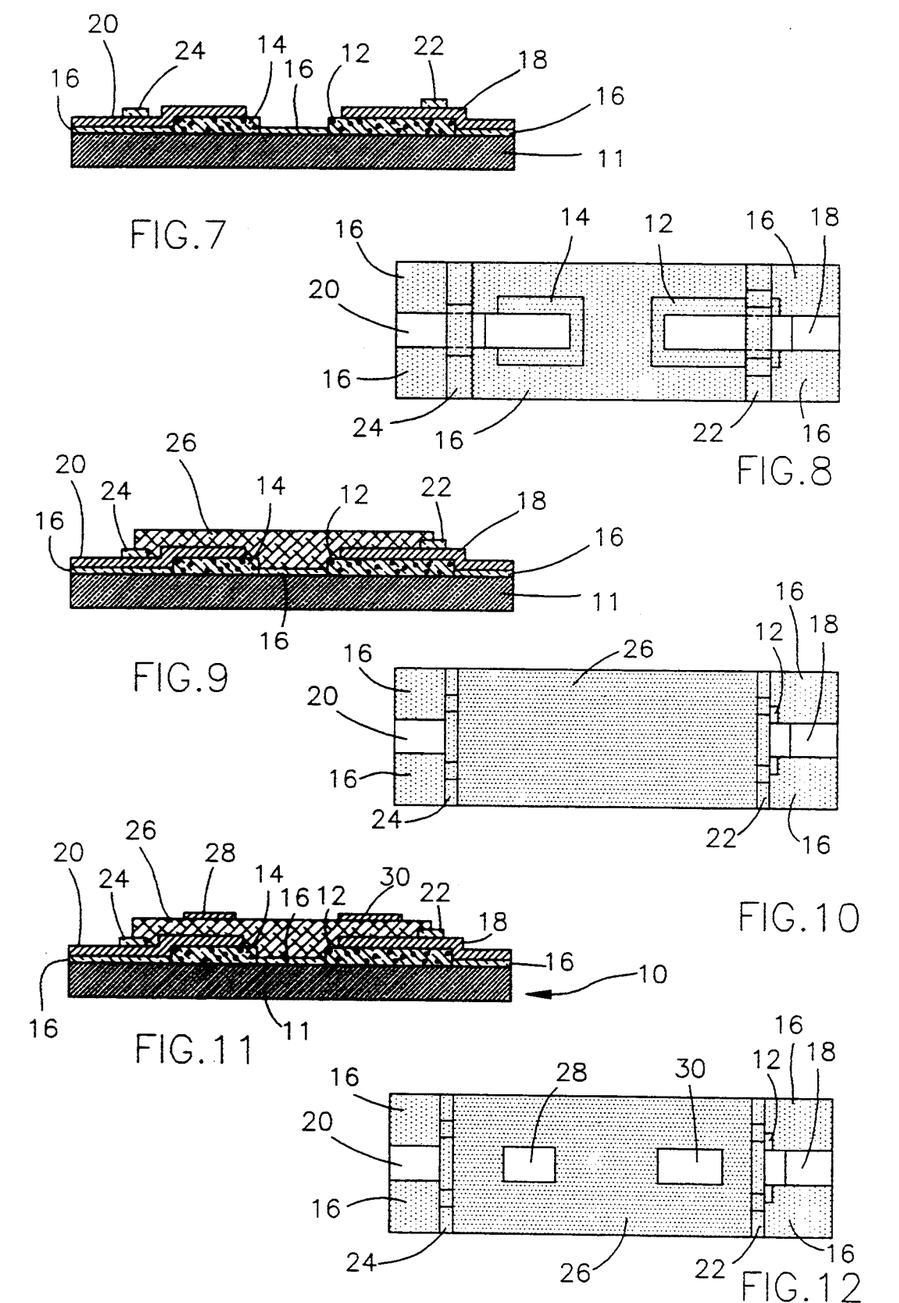
Figure 24:
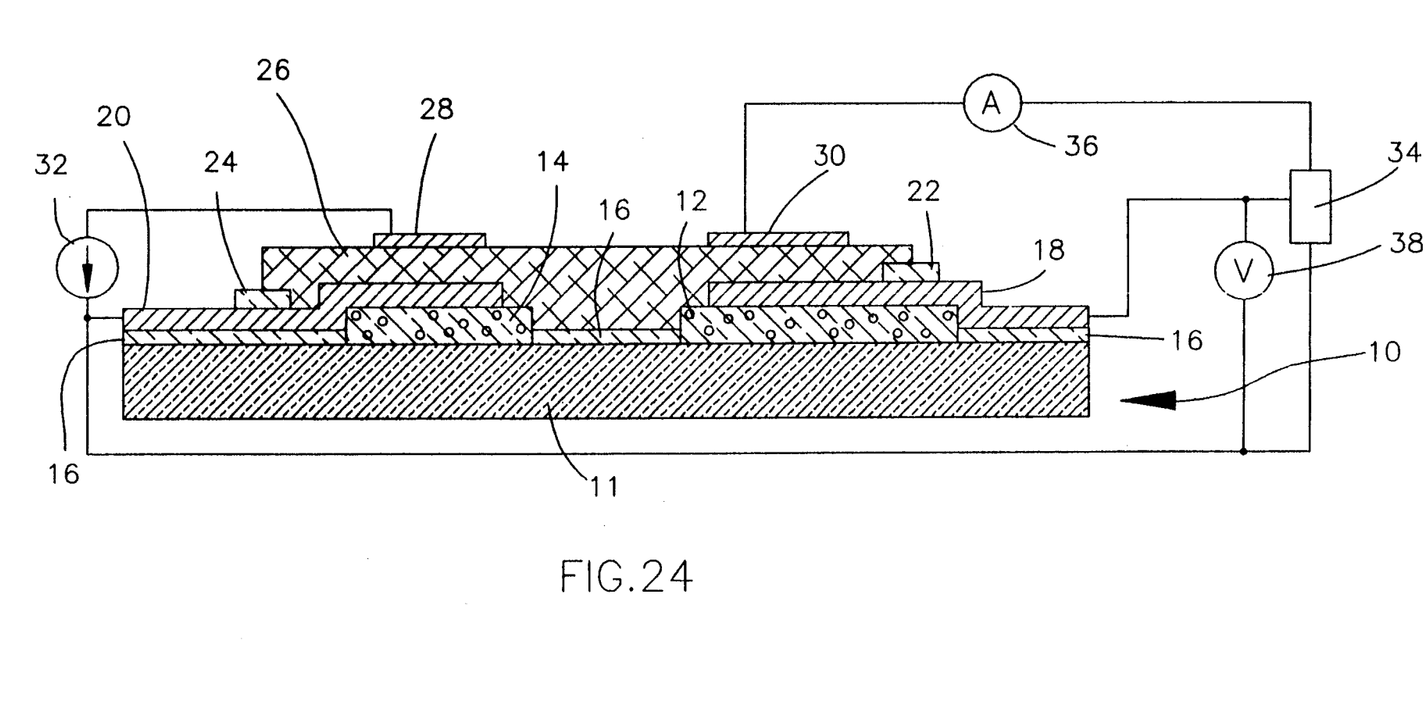
FIG. 24 shows the wide range oxygen sensor of FIGS. 1 through 12 with the addition of electrical circuitry for operating and controlling the wide range oxygen sensor in accordance with this invention.

Referring to FIGS. 11, 12 and 24, there is shown the construction of a wide range oxygen sensor 10 in accordance with a preferred embodiment of this invention. As can be readily seen, the structure of the wide range oxygen sensor 10 is planar and does not include a chamber or recess for use as a gas reference device, as noted with the prior art diffusion limited current oxygen sensors. As will be described more fully below, the wide range oxygen sensor 10 of the present invention instead relies upon the use of porous layers of ceramic to store oxygen as references for determining oxygen partial pressure in the exhaust gas. The wide range oxygen sensor 10 includes a substrate 11 which is preferably formed from dense ceramic, and more preferably dense yttria stabilized zirconia (YSZ) which serves as a barrier to the diffusion of oxygen and other molecules through the wide range oxygen sensor 10. "Dense" in this sense is a relative term indicating that oxygen molecules will not permeate the substrate 11, but instead will diffuse through the more porous oxygen storage layers noted above.

An electrochemical storage cell (14,20,26,28) and an electrochemical pumping cell (12,18,26,30) are formed on the substrate 11 in spaced-apart relation to each other. For illustrative purposes only, in the Figures the electrochemical storage cell (14,20,26,28) is shown to be on the left end of the wide range oxygen sensor 10 while the electrochemical pumping cell (12,18,26,30) is shown to be on the right end of the wide range oxygen sensor 10. However, it will be readily appreciated to one skilled in the art that the locations of the electrochemical storage and pumping cells on the wide range oxygen sensor 10 can be reversed with no effect on the operation of the wide range oxygen sensor 10. The electrochemical storage cell (14,20,26,28) and the electrochemical pumping cell (12,18,26,30) share a solid electrolyte layer 26 formed from a conventional solid electrolyte material, preferably a very dense YSZ. The solid electrolyte layer 26 permits the transfer of oxygen ions therethrough under the influence of an electric current. This arrangement, and particularly the use of a single electrolyte layer, facilitates fabrication of the wide range oxygen sensor 10, thereby reducing manufacturing costs while also enhancing the quality and reliability of the wide range oxygen sensor 10.

Looking first at the completed structure shown in FIGS. 11 and 12, an insulating layer of alumina 16 is preferably provided to discourage ionic flow between the solid electrolyte layer 26 and the substrate 11. "Ionic cross-talk" between the electrochemical storage cell (15,20,26,28) and the electrochemical pumping cell (12,18,26,30) is held to an insignificant level by limiting the thickness of the solid electrolyte layer 26. The relative thinness of the solid electrolyte layer 26 enhances ionic flow through the electrochemical storage and pumping cells and, in conjunction with a sufficient lateral distance between the electrochemical storage and pumping cells, also inhibits ionic transfer between the electrochemical storage and pumping cells. In addition, a pair of insulating band layers 22 and 24 are selectively provided between the solid electrolyte layer 26 and the other elements of the wide range oxygen sensor 10, which are described in detail below, to prevent ionic or electrical leakage at the periphery of the solid electrolyte layer 26.

The electrochemical storage cell includes an upper and lower porous platinum electrode 28 and 20, respectively, disposed on opposite sides of the solid electrolyte layer 26. The porosity of the electrodes 28 and 20 permits the diffusion of oxygen molecules therethrough. An oxygen storage layer 14 is formed from a porous ceramic whose coefficient of thermal expansion closely matches that of the other components of the electrochemical storage cell. The oxygen storage layer 14 is disposed directly on the substrate 11 and contacts the lower electrode 20. "Porous" in this sense is a relative term indicating the ability of the oxygen storage layer 14 to contain oxygen molecules. The porosity of the YSZ oxygen storage layer 14 permits the accumulation and flow of oxygen molecules within the oxygen storage layer 14. The solid electrolyte layer 26 is positioned between the upper and lower porous platinum electrodes 28 and 20 as shown to form an ionic current path between the upper and lower porous platinum electrodes 28 and 20.

As shown in FIG. 24, the electrochemical storage cell (14,20,26,28) is driven by a constant current source 32 to pump oxygen into the oxygen storage layer 14 from the exhaust gas which contacts the upper porous platinum electrode 28 at a rate which is sufficient to maintain a predetermined oxygen partial pressure in the oxygen storage layer 14. In particular, the current from the constant current source 32 must be such that the rate at which oxygen is pumped into the oxygen storage layer 14 is sufficient to compensate for any leakage from the oxygen storage layer 14, which is generally on the order of about 1 to 100 milliamperes. Preferably, the oxygen partial pressure in the oxygen storage layer 14 is within at least one order of magnitude from one atmosphere to provide a stable oxygen partial pressure value. The oxygen partial pressure within the oxygen storage layer 14 of the electrochemical storage cell (14,20,26,28) serves as the reference partial pressure for the operation of the wide range oxygen sensor 10.

The electrochemical pumping cell (12,18,26,30) also has upper and lower porous platinum electrodes 30 and 18, respectively, which are positioned on opposite sides of the solid electrolyte layer 26. The electrochemical pumping cell (12,18,26,30) has a diffusion layer 12 formed from a porous ceramic, according to the same criteria as that of the oxygen storage layer 14, so as to permit the diffusion of oxygen molecules through the diffusion layer 12. The diffusion layer is disposed directly on the substrate 11 and contacts the lower porous platinum electrode 18 of the electrochemical pumping cell's two porous platinum electrodes 18 and 30. As can be seen in FIG. 12, the diffusion layer 12 is partially exposed to the exhaust gases to allow oxygen molecules to diffuse directly into the diffusion layer 12.

The electrochemical pumping cell (12,18,26,30) is driven by a variable voltage source 34 which is connected to the electrochemical pumping cell's porous platinum electrodes 18 and 30 to pump oxygen into and out of the diffusion layer 12 as necessary to maintain a predetermined oxygen partial pressure in the diffusion layer 12. Because the diffusion layer 12 is partially exposed to the exhaust gases, oxygen diffuses laterally into the diffusion layer 12 such that the diffusion layer 12 is predisposed to have an oxygen partial pressure equal to that of the exhaust gas. The porosity and edge geometry of the diffusion layer 12 determines the oxygen diffusion rate into the diffusion layer 12 from this exposed portion. As will be explained more fully in the description of the operation of the wide range oxygen sensor 10, the variable voltage source 34 functions to maintain the oxygen partial pressure in the diffusion layer 12 at a level corresponding approximately to the air/fuel stoichiometric point, instead of the actual partial pressure corresponding to the exhaust gas.

To maintain the proper oxygen partial pressure in the diffusion layer 12, an electrochemical reference cell (20,26,18) is formed by the lower porous platinum electrodes 20 and 18 of the electrochemical storage and pumping cells, respectively. As can be seen in FIG. 11, the solid electrolyte layer 26 also lies between the lower porous platinum electrodes 18 and 20 to complete the ionic circuit of the electrochemical reference cell (20,26,18). The electrochemical reference cell is able to sense the difference in oxygen partial pressures in the oxygen storage layer 14 and the diffusion layer 12. The electrochemical reference cell produces a voltage output based upon the potential difference between the lower porous platinum electrodes 18 and 20 created by the difference in oxygen partial pressure between the diffusion layer 12 and the oxygen storage layer 14. This voltage output, which is shown being detected by a voltmeter 38, can then be used as feedback to the electrochemical pumping cell's variable voltage source 34 such that the electrochemical pumping cell is directed to maintain an oxygen partial pressure in the diffusion layer 12 at a level corresponding approximately to the air/fuel stoichiometric point. In practice, a voltage of approximately 0.45 volts corresponds to the potential difference created between oxygen partial pressure in the diffusion layer 12 at the stoichiometric point and the oxygen partial pressure at one atmosphere or more in the oxygen storage layer 14.

As a result of the voltage supplied across the porous platinum electrodes 18 and 30 of the electrochemical pumping cell by the variable voltage source 34, oxygen ions flow through the electrochemical pumping cell in a direction opposite to the current flow between the porous platinum electrodes 18 and 30. This ionic flow, which is shown being detected by an ammeter 36 in FIG. 24, is proportional to the oxygen concentration in the exhaust gas. The direction of the ionic flow is dependent upon whether the air/fuel mixture is fuel-rich or fuel-lean. If the air/fuel mixture is fuel-rich (i.e., oxygen-poor), the electrochemical pumping cell pumps oxygen ions into the diffusion layer 12 from the upper porous platinum electrode 30 through the solid electrolyte layer 26 and the lower porous platinum electrode 18 so as to compensate for the predisposition of the diffusion layer 12 to have an oxygen partial pressure equal to that of the exhaust gas, which in a fuel-rich condition is less than the oxygen partial pressure at the stoichiometric point of air and fuel. A fuel-lean air/fuel mixture (i.e., oxygen-rich) results in the electrochemical pumping cell pumping oxygen out of the diffusion layer 12 in the opposite direction to that just described.

From the standpoint of manufacturing, the use of a single solid electrolyte layer 26 has the advantage of being simpler to fabricate when compared to multiple electrolyte layers. Moreover, multiple electrolyte layers contribute to functional problems because the oxygen partial pressure in the diffusion layer 12 would be measured in a different location than where oxygen is pumped in and out of the diffusion layer 12. The wide range oxygen sensor 10 of the present invention takes advantage of the properties of the single solid electrolyte layer 26 to simplify the sensor's structure. It has been determined that by limiting the thickness of the solid electrolyte layer 26, the ionic resistance between the electrodes of each individual cell (i.e., between the upper porous platinum electrodes 28 and 30 and their respective lower porous platinum electrodes 20 and 18) is much lower than that between each horizontally-spaced pair of electrodes (i.e., between the lower porous platinum electrodes 20 and 18 and between the upper porous platinum electrodes 30 and 28). As a result, the ionic leakage current between the horizontally-spaced pairs of electrodes (i.e., between the lower porous platinum electrodes 18 and 20, and between the upper porous platinum electrodes 28 and 30) is small compared to the pumping currents within the electrochemical storage and pumping cells. As a result, any sensor error caused by ionic cross-talk between the electrochemical storage and pumping cells is negligible. The potential between the lower porous platinum electrodes 18 and 20 can be measured even with the high resistance between the lower porous platinum electrodes 18 and 20 because no significant ionic flow between the lower porous platinum electrodes 18 and 20 is required.

The preferred processing steps for forming the wide range oxygen sensor 10 are illustrated in FIGS. 1 through 12. First, as shown in cross-section in FIG. 1 and as a plan view in FIG. 2, the oxygen storage layer 14 and the diffusion layer 12 are deposited to a depth of about 25 microns to about 200 microns on the substrate 11. The oxygen storage layer 14 and the diffusion layer 12 are preferably deposited using known screen printing methods, and are then fired in a furnace at temperatures of approximately 1300° to 1500° C. The distance between the oxygen storage layer 14 and the diffusion layer 12 is about 3 to about 5 millimeters to limit ionic cross-talk therebetween. Alternatively, the oxygen storage layer 14 and the diffusion layer 12 can be formed on the substrate 11 by compressing a porous ceramic/polymer tape (corresponding to the oxygen storage layer 14 and the diffusion layer 12) to a dense ceramic/polymer tape (corresponding to the substrate 11) at locations in the surface of the substrate 11 at which the oxygen storage and diffusion layers 14 and 12 are to be formed. Such ceramic/polymer tapes are well known in the art and are formed using known ceramic tape casting methods. The structure is then fired to dissipate the binder, leaving a porous ceramic layer bonded to the dense YSZ substrate 11.

Figures 1, 2, 3, 4, 5:
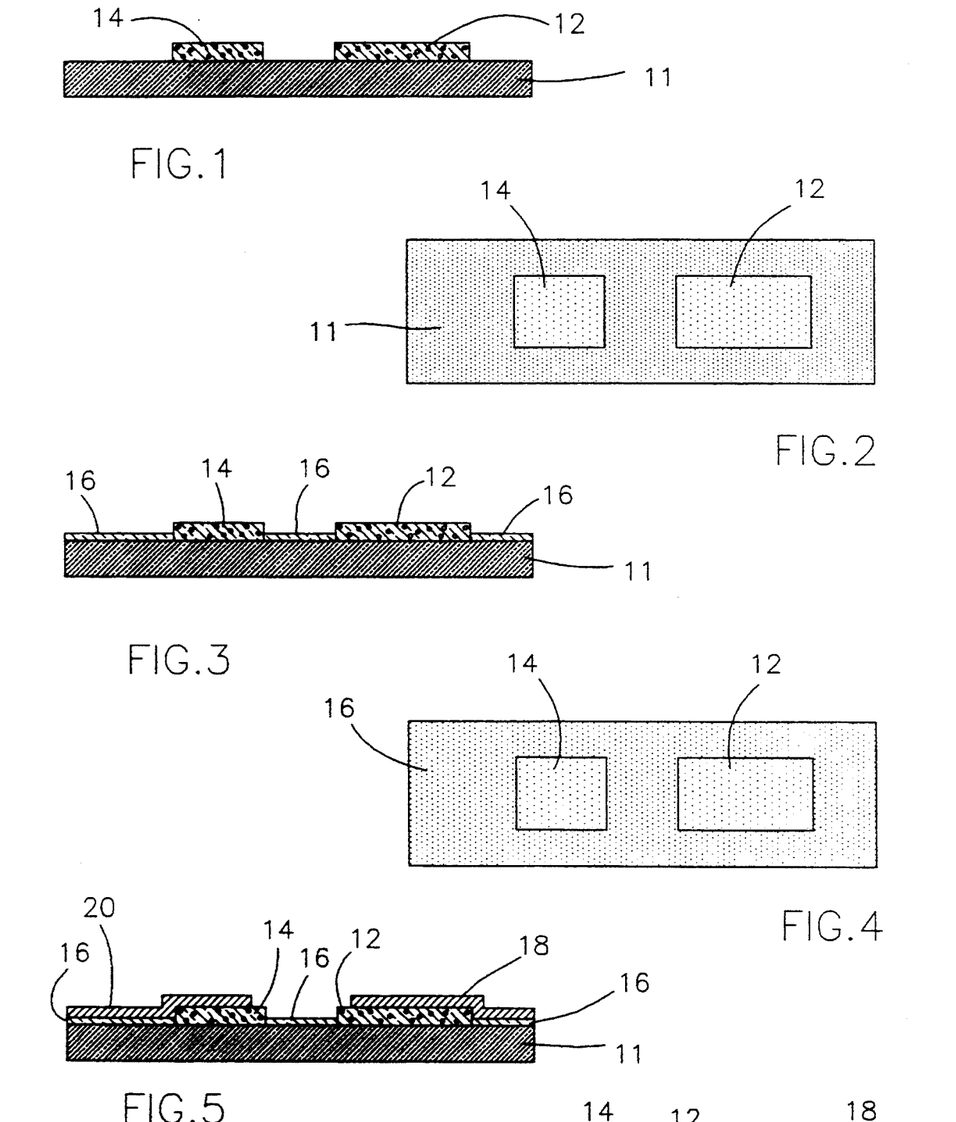
FIGS. 1 through 12 show the processing steps in the manufacture of a wide range oxygen sensor in accordance with a preferred embodiment of this invention, wherein the odd numbered Figures show the processing steps in cross-section while the even numbered Figures show the processing steps in plan view.

As shown in FIGS. 3 and 4, the insulating alumina layer 16 is then deposited through a suitably sized mask to a depth of about 20 microns using known plasma spray deposition techniques, though other known methods, such as screen printing, could be foreseeably used to achieve similar results. The thickness of this insulating layer can vary from submicron size to about 50 microns, since its function is to prevent deleterious ionic or electrical communication with the substrate 11. The masking technique permits the insulating layer 16 to be selectively deposited on the substrate 11 as shown in FIG. 2 to the exclusion of the oxygen storage layer 14 and the diffusion layer 12.

Figure 6:
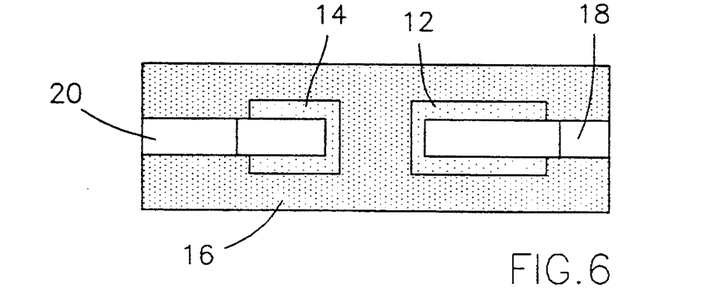

With reference now to FIGS. 5 and 6, the lower porous platinum electrodes 18 and 20 are then deposited onto the insulating layer through a mask to a depth of about 1 microns to about 1.5 microns. The lower porous platinum electrodes 18 and 20 are preferably deposited using known sputtering techniques. As shown in FIGS. 5 and 6, each of the lower porous platinum electrodes 18 and 20 is in contact with its corresponding diffusion layer 12 and oxygen storage layer 14. The insulating band layers 22 and 24 are then formed across the width of the wide range oxygen sensor 10, as shown in FIGS. 7 and 8, again using known plasma spray techniques or other known methods with a mask to selectively deposit the insulating band layers 22 and 24 as shown to a depth of about 20 microns. In addition, these insulating bands, which are also preferably formed from alumina, may range in thickness from submicron size to about 50 microns since their function is to prevent ionic or electrical leakage at the periphery of the solid electrolyte layer 26. Specifically, the insulating band layers 22 and 24 serve to eliminate the formation of a triple point formed where the electrodes 18 and 20 contact the exhaust gas, which would otherwise create a leakage path for oxygen ions into or out of the solid electrolyte layer 26. The resulting ionic current would add to or subtract from the pumping current, thereby creating an output error. The insulating band layer 22 corresponding to the electrochemical pumping cell is located on the wide range oxygen sensor 10 such that the diffusion layer 12 is partially exposed to permit diffusion of oxygen directly into the diffusion layer 12, as can best be seen in FIG. 8.

As shown in FIGS. 9 and 10, the solid electrolyte layer 26 is then formed by plasma spray deposition to cover essentially all of the upper surface of the wide range oxygen sensor 10 between the insulating band layers 22 and 24. As a result, the lower porous platinum electrodes 18 and 20 are partially left exposed to serve as contacts. In addition, the solid electrolyte layer 26 leaves the diffusion layer 12 partially exposed to permit diffusion of oxygen directly into the diffusion layer 12, as can best be seen in FIG. 10. The thickness of the solid electrolyte layer 26 preferably ranges between about 100 microns and about 500 microns. This thickness is sufficiently small relative to the distance between the oxygen storage layer 14 and the diffusion layer 12 to minimize ionic cross-talk between the oxygen storage layer 14 and the diffusion layer 12. Finally, the upper porous platinum electrodes 28 and 30 are sputtered onto the solid electrolyte layer 26 such that each is in ionic communication with its corresponding lower porous platinum electrode 20 and 18, respectively, as shown in FIGS. 11 and 12.

The operation of the wide range oxygen sensor 10 is as follows. As described above, the electrochemical storage cell seeks to maintain an oxygen partial pressure in the oxygen storage layer 14 within at least one order of magnitude from one atmosphere to provide a stable oxygen partial pressure reference value. The constant current source 32 of the electrochemical storage cell creates a current flow from the lower porous platinum electrode 20 through the solid electrolyte layer 26 to the upper porous platinum electrode 28. This causes the oxygen molecules in the exhaust gases adjacent to the upper porous platinum electrode 28 to ionize. Because oxygen ions are negatively charged, the ions diffuse through the solid electrolyte layer 26 and into the oxygen storage layer 14 where they give up their excess electrons and recombine to form oxygen molecules within the oxygen storage layer 14.

In contrast, the electrochemical pumping cell seeks to maintain the diffusion layer 12 with an oxygen partial pressure approximately equal to the oxygen partial pressure at the stoichiometric point for the particular air/fuel mixture. If the engine is operating at the stoichiometric point, the oxygen which naturally diffuses into the diffusion layer 12 at its exposed surface will establish an oxygen partial pressure within the diffusion layer 12 substantially equal to the oxygen partial pressure at the stoichiometric point. The difference in oxygen partial pressures in the oxygen storage layer 14 and the diffusion layer 12 will establish a voltage in the electrochemical reference cell (i.e., between the lower porous platinum electrodes 20 and 18, respectively) of about 450 millivolts.

However, where the engine is operating in a fuel-rich or fuel-lean condition, the diffusion layer 12 will be predisposed to have an oxygen partial pressure less than or greater than that at the stoichiometric point, respectively. If the engine is operating in the fuel-rich condition, the potential between the lower porous platinum electrodes 18 and 20 will be higher than 450 millivolts due to oxidizable gases, such as carbon monoxide, hydrogen and hydrocarbons, diffusing through the diffusion layer 12 and creating a very low equilibrated oxygen partial pressure. As a result, a feedback signal from the electrochemical reference cell will be relayed to the variable voltage source 34 which regulates the voltage across the porous platinum electrodes 30 and 18 of the electrochemical pumping cell. To increase the oxygen partial pressure in the diffusion layer 12 to reestablish the 450 millivolts potential, the variable voltage source 34 will create a potential between the lower and upper porous platinum electrodes 18 and 30 of the electrochemical pumping cell that creates a current flow from the lower porous platinum electrode 18 to the upper porous platinum electrode 30. As a result, oxygen molecules will be ionized at the upper porous platinum electrode 30 and flow through the solid electrolyte layer 26 to the diffusion layer 12, the effect of which is to increase the oxygen partial pressure in the diffusion layer 12. The current flow necessary to maintain the oxygen partial pressure in the diffusion layer 12 at the stoichiometric point will be proportional to the concentration of oxidizable gases present, or fully equilibrated oxygen partial pressure, in the exhaust gases according to the diffusion current limiting mode.

Similarly, if the engine is operating in the fuel-lean condition, the potential between the lower porous platinum electrodes 18 and 20 will be lower than 450 millivolts. As a result, the feedback signal from the electrochemical reference cell to the variable voltage source 34 will cause a reversal of the polarity as compared to the fuel-rich operation in order to decrease the oxygen partial pressure in the diffusion layer 12 and reestablish the 450 millivolts potential. The potential created by variable voltage source 34 between the lower and upper porous platinum electrodes 18 and 30 will create a current flow from the upper porous platinum electrode 30 to the lower porous platinum electrode 18. As a result, oxygen molecules will be ionized in the diffusion layer 12 at the lower porous platinum electrode 18 and flow through the solid electrolyte layer 26 to the upper porous platinum electrode 30, the effect of which is to decrease the oxygen partial pressure in the diffusion layer 12. Again, the current flow necessary to maintain the oxygen partial pressure in the diffusion layer 12 at the stoichiometric point will be proportional to the oxygen partial pressure in the exhaust gases according to the diffusion current limiting mode.

Figures 19, 20, 21:
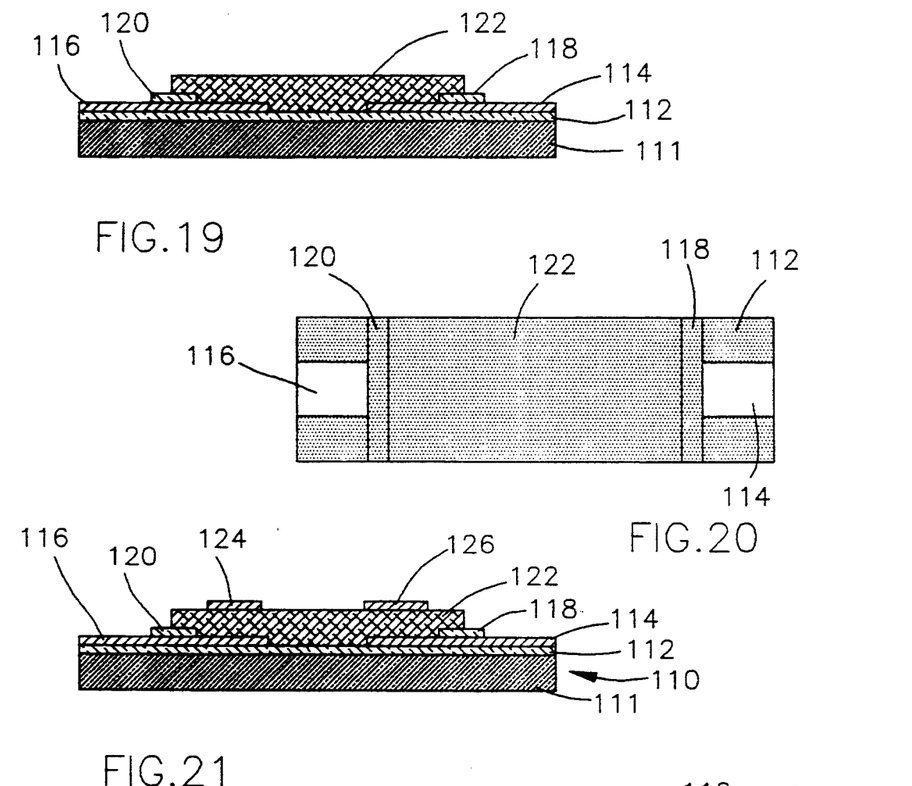
Figure 22:
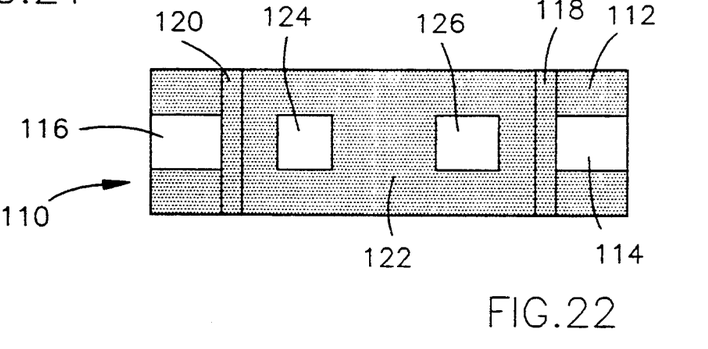

An alternative embodiment of a wide range oxygen sensor 110 which also operates partially in the diffusion current limiting mode and which can also be characterized as being readily manufacturable in accordance with this invention is shown in FIGS. 21 and 22. This alternative embodiment also includes a dense ceramic substrate 111, an electrochemical storage cell and an electrochemical pumping cell disposed on the substrate 111 in spaced-apart relation to each other, and an electrochemical reference cell formed between the electrochemical storage and pumping cells. As with the preferred embodiment, the electrochemical storage and pumping cells share a single YSZ electrolyte layer so as to facilitate processing and thereby reduce manufacturing costs. However, this embodiment does not employ distinct porous layers for forming an oxygen storage layer or a diffusion layer, but instead uses a porous YSZ electrolyte layer layer 122, enabling the wide range oxygen sensor 110 to rely upon the pores and cracks in the porous electrolyte layer 122 for purposes of both oxygen storage and diffusion.

As with the preferred embodiment, the electrochemical storage cell (116,122,124) has upper and lower porous platinum electrodes 124 and 116, respectively, disposed on opposite sides of the porous electrolyte layer 122. An oxygen storage region exists in the porous electrolyte layer 122 adjacent to the lower porous platinum electrode 116. The electrochemical pumping cell (114,122,126) also has upper and lower porous platinum electrodes 126 and 114, respectively, positioned on opposite sides of the porous electrolyte layer 122. Similar to the oxygen storage region of the electrochemical storage cell, the electrochemical pumping cell has a diffusion region in the porous electrolyte layer 122 adjacent to the lower porous platinum electrode 114. As with the preferred embodiment, an electrochemical reference cell (116,122,114) is formed between the lower porous platinum electrodes 116 and 114 of the electrochemical storage and pumping cells, and serves to monitor the oxygen partial pressure in the diffusion region relative to the predetermined oxygen partial pressure in the oxygen storage region.

To prevent ionic and current leakage to the substrate 111, the porous electrolyte layer 122 and the electrochemical storage and pumping cells are deposited upon a ceramic layer 112. In addition, a pair of insulating band layers of ceramic 118 and 120 extend across the width of the wide range oxygen sensor 110 to prevent the leakage of oxygen ions along the interface between the porous electrolyte layer 122 and the lower porous platinum electrodes 116 and 114.

Figure 13:
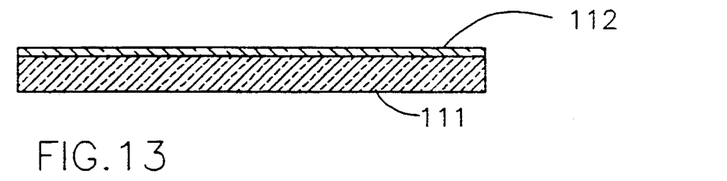
FIGS. 13 through 22 show the processing steps in the manufacture of a wide range oxygen sensor in accordance with a second embodiment of this invention, wherein the odd numbered Figures show the processing steps in cross-section while the even numbered Figures show the processing steps in plan view.
Figure 14:
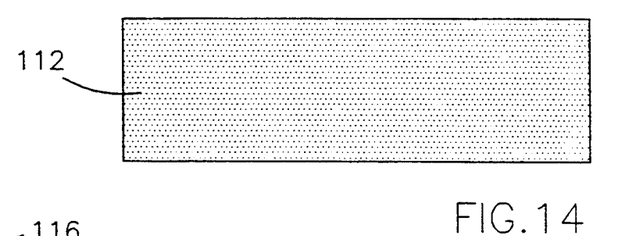
Figures 15, 16, 17, 18:
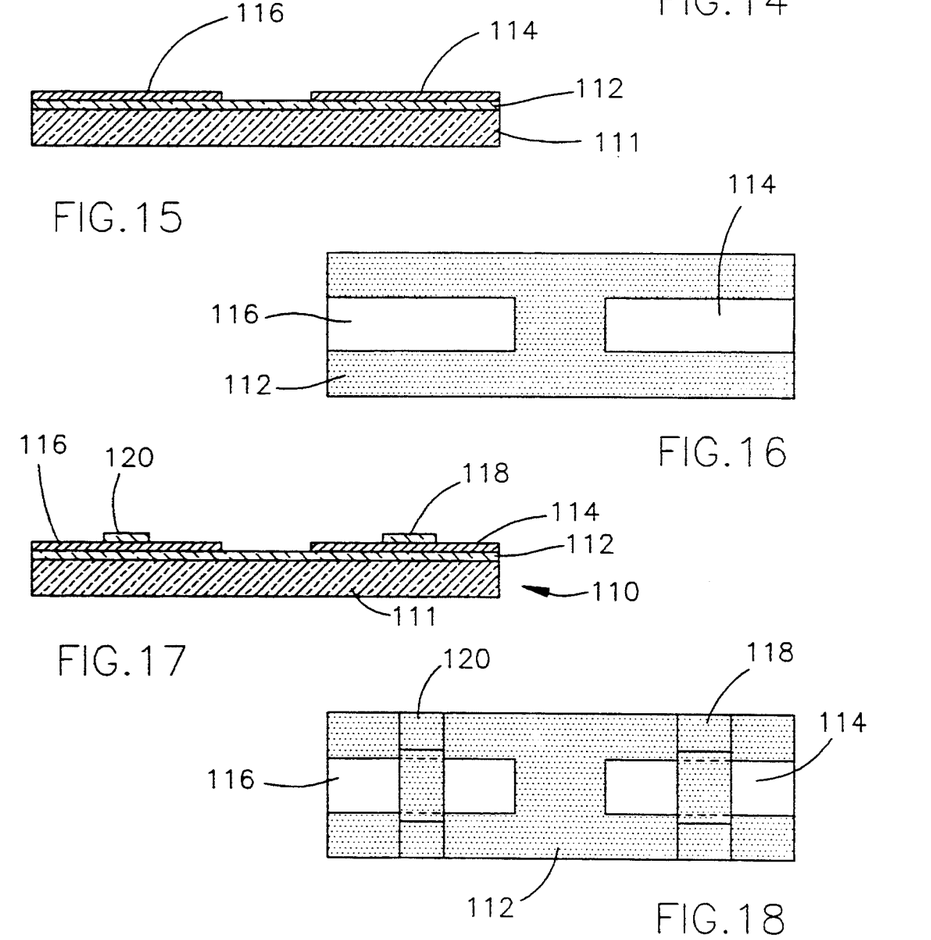

The operation of the wide range oxygen sensor 110 is essentially identical to the wide range oxygen sensor 10 of the preferred embodiment of FIGS. 1 through 12. However, as seen in FIGS. 13 through 22, the processing of the wide range oxygen sensor 110 differs from that of the preferred embodiment as follows. As shown in FIGS. 13 and 14, the ceramic (preferably alumina) insulating layer 112 is first deposited over the entire surface of the substrate 111 to a depth of about 20 microns using known plasma spray deposition techniques though, as before, other known methods such as screen printing could be foreseeably used to achieve similar results. The thickness can again vary between submicron size and about 50 microns, since its function is to prevent deleterious ionic or electrical communication with the substrate 111. With reference to FIGS. 15 and 16, the lower porous platinum electrodes 116 and 114 are then deposited onto the insulating layer through a mask to a depth of about 1 microns to about 1.5 microns. The porous platinum electrodes 116 and 114 are preferably deposited using known sputtering techniques. The insulating band layers 120 and 118 are then formed across the width of the wide range oxygen sensor 110, as shown in FIGS. 17 and 18, again using known plasma spray techniques with a mask to selectively deposit the insulating band layers 120 and 118 to a depth of about 20 microns.

Referring to FIGS. 19 and 20, the porous electrolyte layer 122 is then formed by plasma spray deposition to cover essentially all of the upper surface of the wide range oxygen sensor 110 between the insulating band layers 120 and 118. The thickness of the porous electrolyte layer 122 is preferably about 100 microns to about 500 microns. Finally, the upper porous platinum electrodes 124 and 126 are sputtered onto the porous electrolyte layer 122 such that each is in ionic communication with its corresponding lower porous platinum electrode 116 and 114, respectively, as shown in FIGS. 21 and 22.

Figure 23:
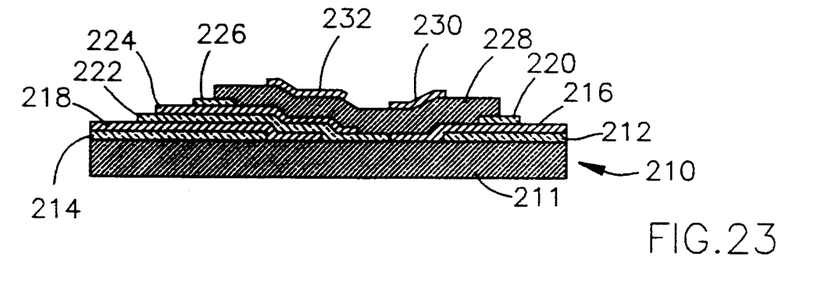
FIG. 23 shows in cross-section a wide range oxygen sensor in accordance with a third embodiment of this invention.

A third embodiment of a wide range oxygen sensor 210 which operates in the diffusion current limiting mode in accordance with this invention is shown in FIG. 23. This embodiment also includes a dense ceramic, and preferably YSZ, substrate 211, an electrochemical storage cell (224,228,232) and an electrochemical pumping cell (216,228,230) disposed on the substrate 211 in spaced-apart relation to each other, and an electrochemical reference cell (218,211,216) formed between the electrochemical storage and pumping cells. The electrochemical storage cell operates between porous platinum electrodes 224 and 232 and the electrochemical pumping cell operates between porous platinum electrodes 216 and 230. As with the preferred embodiment, the electrochemical storage and pumping cells share a single plasma sprayed YSZ electrolyte layer 228 so as to facilitate processing and thereby also reduce manufacturing costs. However, this embodiment employs a fifth porous platinum electrode 218 for the purpose of avoiding the effect of polarization of the lower electrode 224 of the electrochemical storage cell.

Structurally as seen in FIG. 23, the difference between the 4-electrode structure of the first and second embodiments and the 5-electrode structure of this embodiment is that the electrochemical reference cell is isolated from the electrochemical oxygen storage cell. Referring to the first embodiment of FIG. 11 for illustrative purposes, the electrochemical pumping cell operates between lower and upper porous platinum electrodes 18 and 30, and the electrochemical reference cell operates between lower porous platinum electrodes 18 and 20—thus, the electrochemical pumping cell and reference cell share electrode 18. As a result, polarization effects due to pumping can impact the voltage generated by the electrochemical reference cell. To avoid this effect, the fifth electrode 218 is added to form the reference cell between electrodes 218 and 216. The electrode 218 is exposed to the oxygen in the oxygen storage layer 222, but there is not an electronic connection to electrode 224 of the electrochemical storage cell. The advantage of this embodiment is potentially improved performance, though the structure is somewhat more complex.

As seen in FIG. 23, both of the lower electrodes 218 and 216 contact the YSZ substrate 211, permitting the YSZ substrate 211 to serve as the electrolyte for the electrochemical reference cell formed between the lower electrodes 218 and 216. Simultaneously, the lower electrode 218 is exposed directly to the stored oxygen within the oxygen storage layer 222. Similar to the first and second embodiments, alumina insulating layers 212, 214, 220 and 226 are provided and function as described previously.

Alternatively, a 5-electrode structure can be formed by depositing a plasma sprayed YSZ electrolyte layer in place of using the YSZ substrate as a second electrolyte layer. Essentially, a first YSZ electrolyte layer would be deposited between the electrodes 218 and 224 to serve as the oxygen storage layer 222 as well as the electrolyte for the electrochemical reference cell. A second YSZ electrolyte layer would then be deposited between the electrodes 218 and 216 and over the electrodes 224 and 216 to serve as the electrolyte for the electrochemical storage and pumping cells between the electrodes 224 and 232, and 216 and 230, respectively.

From the above, it can be seen that a significant advantage of the present invention is that the construction of the wide range oxygen sensors 10, 110 and 210 and the processing methods serve to reduce manufacturing costs while also making the wide range oxygen sensors 10, 110 and 210 more readily producible under mass production conditions. Specifically, each of the embodiments is fabricated with a planar horizontal structure which does not require the reference gas chambers noted with the prior art. Accordingly, manufacturing and fabrication constraints associated with the need for complicated geometries are overcome. In addition, the planar configuration of the wide range oxygen sensors 10, 110 and 210 of the present invention permit the use of thermal deposition methods which advantageously facilitate mass production.

Processing of the wide range oxygen sensors 10, 110 and 210 is also facilitated by using a single electrolyte layer which is advantageous in that it simplifies fabrication as compared to the need to deposit multiple electrolyte layers. Moreover, the use of a single electrolyte layer overcomes various disadvantages associated with multiple electrolyte layers. As an example, multiple electrolyte layers generally create operational problems because the oxygen partial pressure in the diffusion layer is measured in a different location than where oxygen is pumped in and out of the diffusion layer. The wide range oxygen sensors 10, 110 and 210 of the present invention are able to avoid the potential disadvantage of ionic cross-talk by exploiting the properties of the electrolyte layer. Specifically, by limiting the thickness of the electrolyte layer, the ionic resistance between the electrodes of each individual cell (i.e., between the upper electrodes and their respective lower electrodes) is much lower than that between each horizontally-spaced pair of electrodes (i.e., between the lower electrodes and between the upper electrodes). As a result, the ionic leakage current between the horizontally-spaced pairs of electrodes is small compared to the pumping currents within the electrochemical storage and pumping cells. Therefore, any sensor error caused by ionic cross-talk between the electrochemical storage and pumping cells is negligible.

Another significant advantage of the present invention is that the wide range oxygen sensors 10, 110 and 210 each operate partially in the diffusion limited current mode, resulting in an output which is proportional to the oxygen partial pressure in the exhaust gases. As a result, the wide range oxygen sensors 10, 110 and 210 are capable of accurately determining the oxygen partial pressure in the exhaust gas of engines operating under both fuel-rich and fuel-lean conditions is desirable. Such an operating mode is superior to potentiometric oxygen sensors with respect to fuel utilization and emissions control by having sufficient sensitivity to accurately determine the oxygen partial pressure in both the fuel-rich and fuel-lean conditions.

Therefore, while our invention has been described in terms of a preferred embodiment, it is apparent that other forms could be adopted by one skilled in the art, for example by modifying the processing methods used, or by substituting appropriate electrolyte and insulating materials. Accordingly, the scope of our invention is to be limited only by the following claims.

The embodiments of the invention in which an exclusive property or privilege is claimed are defined as follows:

1. An oxygen sensor for sensing an oxygen concentration in a gas, said oxygen sensor comprising:
    a substrate;
    a storage cell disposed on said substrate, said storage cell having first and second electrodes, an electrolyte layer disposed between said first and second electrodes, and an oxygen storage layer contacting said second electrode, such that when a current flows between said first and second electrodes said storage cell pumps oxygen from an oxygen source through said electrolyte layer and into said oxygen storage layer so as to maintain a first predetermined oxygen partial pressure in said oxygen storage layer;
    a pumping cell disposed on said substrate, said pumping cell having third and fourth electrodes and a diffusion layer, said electrolyte layer being disposed between said third and fourth electrodes, said diffusion layer contacting the gas such that the oxygen within the gas diffuses into said diffusion layer so as to establish an oxygen partial pressure in said diffusion layer, such that when a current flows between said third and fourth electrodes said pumping cell pumps and from the gas through said electrolyte layer and out of and into said diffusion layer, respectively, so as to maintain a second predetermined oxygen partial pressure in said diffusion layer;
    said electrolyte layer being sufficiently thin so as to enhance ionic flow between said first and second electrodes of said storage cell and between said third and fourth electrodes of said pumping cell while said pumping cell is sufficiently spaced apart from said storage cell so as to inhibit ionic flow therebetween through said electrolyte layer; and
    a reference cell formed between said storage and pumping cells so as to produce an output in response to a difference between said first predetermined pressure in said oxygen storage layer and said pressure in said diffusion layer;
    whereby said output of said reference cell can be used to regulate said pumping cell such that said pumping cell pumps oxygen into and out of said diffusion layer so as to establish said second predetermined oxygen partial pressure in said diffusion layer, said current flowing through said pumping cell thereby corresponding to the oxygen concentration in the gas.

2. An oxygen sensor as recited in claim 1 wherein said electrolyte comprises an yttria stabilized zirconia solid electrolyte layer.

3. An oxygen sensor as recited in claim 1 wherein said oxygen storage layer is a porous alumina layer deposited upon said substrate.

4. An oxygen sensor as recited in claim 1 wherein said diffusion layer is a porous alumina layer deposited upon said substrate.

5. An oxygen sensor as recited in claim 1 wherein said first, second, third and fourth electrodes are porous platinum.

6. An oxygen sensor as recited in claim 1 wherein said substrate is a dense yttria stabilized zirconia substrate.

7. An oxygen sensor as recited in claim 1 wherein said first predetermined oxygen partial pressure is within at least one order of magnitude from one atmosphere.

8. An oxygen sensor as recited in claim 1 wherein said reference cell is formed between said second and fourth electrodes.

9. A wide range air/fuel ratio sensor for sensing an oxygen concentration in an exhaust gas, said oxygen sensor comprising:
    a substrate;
    a first porous layer deposited on said substrate said first porous layer defining an oxygen storage layer of an electrochemical storage cell.;
    a second porous layer deposited on said substrate and spaced from said oxygen storage layer, said second porous layer defining a diffusion layer of an electrochemical pumping cell;
    a solid electrolyte layer deposited on both said oxygen storage layer and said diffusion layer so as to form electrolyte layer for both said electrochemical storage cell and said electrochemical pumping cell, said solid electrolyte layer being sufficiently thin so as to enhance ionic flow through said electrochemical storage cell and through said electrochemical pumping cell while said electrochemical pumping cell is sufficiently spaced apart from said electrochemical storage cell so as to inhibit ionic flow therebetween through said solid electrolyte layer;
    a first pair of electrodes associated with said electrochemical storage cell, a first electrode of said first pair of electrodes contacting both the exhaust gas and said solid electrolyte layer, a second electrode of said first pair of electrodes contacting both said solid electrolyte layer and said oxygen storage layer;
    a second pair of electrodes associated with said electrochemical pumping cell, a first electrode of said second pair of electrodes contacting said solid electrolyte layer, a second electrode of said second pair of electrodes contacting both said solid electrolyte layer and said diffusion layer, said diffusion layer contacting the exhaust gas such that the oxygen within the exhaust gas diffuses into said diffusion layer so as to establish an oxygen partial in said diffusion layer;
    a current source generating a current between said first and second electrodes of said electrochemical storage cell so as to pump oxygen from said exhaust gas through said solid electrolyte layer and into said oxygen storage layer such that a first predetermined oxygen partial pressure is maintained in said oxygen storage layer.;

a variable voltage source generating a current between said first and second electrodes of said electrochemical pumping cell so as to pump. Oxygen to and from said exhaust gas through said solid electrolyte layer and out of and into said diffusion layer, respectively, said current between said first and second electrodes of said electrochemical pumping cell being substantially proportional to the oxygen concentration in the exhaust gas;

an electrochemical reference cell formed between said electrochemical storage cell and said electrochemical pumping cell so as to produce an output in response to a difference between said first predetermined oxygen partial pressure in said oxygen storage layer and said oxygen partial pressure in said diffusion layer; and a feedback circuit for regulating said electrochemical pumping cell based on said output of said electrochemical reference cell such that said electrochemical pumping cell maintains a second predetermined oxygen partial pressure in said diffusion layer at a level approximately equal to a predetermined air/fuel stoichiometric point.

10. An oxygen sensor as recited in claim 9 wherein said first and second electrodes of said first and second pairs of electrodes are porous platinum.

11. An oxygen sensor as recited in claim 9 wherein said substrate is a dense yttria stabilized zirconia substrate.

12. An oxygen sensor as recited in claim 9 wherein first predetermined oxygen partial pressure is within at least one order of magnitude from one atmosphere.

13. An oxygen sensor as recited in claim 9 wherein said current source is a constant current source connected to said first and second electrodes of said electrochemical storage cell, said constant current source generating said current between said first and second electrodes of said electrochemical storage cell so as to maintain said first predetermined oxygen partial pressure in said oxygen storage layer.

14. An oxygen sensor as recited in claim 9 further comprising an insulating layer deposited on said substrate between said first and second porous layers so as to define an insulating member therebetween.

15. An oxygen sensor as recited in claim 9 wherein the distance between said first and second electrodes of each said first and second pair of electrodes is substantially less than the distance between said first and second porous layers so as to minimize ionic cross-talk therebetween.

16. An oxygen sensor as recited in claim 9 wherein said electrochemical reference cell is formed between said second electrode of said first pair of electrodes and said second electrode of said second pair of electrodes.

* * * * *